US010094804B2

(12) United States Patent
Murakoshi et al.

(10) Patent No.: US 10,094,804 B2
(45) Date of Patent: Oct. 9, 2018

(54) BIOLOGICAL INFORMATION MEASUREMENT DEVICE AND METHOD FOR CONTROLLING BIOLOGICAL INFORMATION MEASUREMENT DEVICE

(71) Applicant: PHC Holdings Corporation, Minato-ku, Tokyo (JP)

(72) Inventors: Soichiro Murakoshi, Ehime (JP); Yoichi Tanizaki, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 90 days.

(21) Appl. No.: 15/115,910

(22) PCT Filed: Mar. 9, 2015

(86) PCT No.: PCT/JP2015/056845
§ 371 (c)(1),
(2) Date: Aug. 2, 2016

(87) PCT Pub. No.: WO2015/141510
PCT Pub. Date: Sep. 24, 2015

(65) Prior Publication Data
US 2017/0131232 A1    May 11, 2017

(30) Foreign Application Priority Data

Mar. 20, 2014  (JP) .................................. 2014-058587

(51) Int. Cl.
*G01N 27/416*      (2006.01)
*G01N 33/66*       (2006.01)
(Continued)

(52) U.S. Cl.
CPC ..... *G01N 27/4163* (2013.01); *G01N 27/3274* (2013.01); *G01N 33/66* (2013.01)

(58) Field of Classification Search
CPC .. G01N 22/4163; G01N 27/416; G01N 27/26; G01N 33/00; G01N 27/4163
(Continued)

(56) References Cited

U.S. PATENT DOCUMENTS

| 6,880,968 B1 | 4/2005 | Haar | |
| 2003/0207442 A1* | 11/2003 | Markovsky | A23D 9/00 435/287.2 |

(Continued)

FOREIGN PATENT DOCUMENTS

| JP | H04-122852 A | 4/1992 |
| JP | 2001-337066 A | 12/2001 |

(Continued)

OTHER PUBLICATIONS

Internationanl Search Report of corresponding PCT Application No. PCT/JP2015/056845 dated Apr. 21, 2015.
(Continued)

*Primary Examiner* — Christine T Mui
(74) *Attorney, Agent, or Firm* — Shinjyu Global IP (57) ABSTRACT

Implementations relate to a biological information measurement device, and it is an object thereof to perform appropriate measurement. To achieve this object, a biological information measurement device may comprise a main body case, a connector, a measurement component, a cover, and an external temperature measurement component. The main body case has a sensor insertion opening into which a sensor is inserted. The connector is provided on the inside of the sensor insertion opening inside the main body case, and is electrically connected to the sensor inserted in the sensor insertion opening. The measurement component is electrically connected to the connector. The cover is provided on the surface of the main body case and openably and closeably covers the sensor insertion opening. The external
(Continued)

temperature measurement component is provided on the surface of the main body case and measures the temperature of the air outside the main body case.

14 Claims, 7 Drawing Sheets

(51) Int. Cl.
G01N 27/327 (2006.01)
G01N 33/00 (2006.01)

(58) Field of Classification Search
USPC ............... 436/95, 94, 93, 91; 347/142, 141; 49/13; 422/50, 82.01, 82.03
See application file for complete search history.

(56) References Cited

U.S. PATENT DOCUMENTS

| | | |
|---|---|---|
| 2005/0019219 A1 | 1/2005 | Oshiman et al. |
| 2012/0116706 A1 | 5/2012 | Nakanishi et al. |
| 2013/0197847 A1 | 8/2013 | Tsukada et al. |
| 2014/0012116 A1 | 1/2014 | Okuyama |
| 2014/0177671 A1 | 6/2014 | Watanabe |

FOREIGN PATENT DOCUMENTS

| | | | |
|---|---|---|---|
| JP | 2003-513277 A | 4/2003 | |
| JP | 2006-198321 A | 8/2006 | |
| WO | 2003/062812 A1 | 7/2003 | |
| WO | 2011/001917 A1 | 1/2011 | |
| WO | 2011/105178 A1 | 9/2011 | |
| WO | WO 2012/027583 A2 * | 3/2012 | ............ G01N 21/31 |
| WO | 2012/127870 A1 | 9/2012 | |
| WO | 2013/014944 A1 | 1/2013 | |

OTHER PUBLICATIONS

Internationanl Preliminary Examination Report of corresponding PCT Application No. PCT/JP2015/056845 dated Aug. 19, 2015.

* cited by examiner

BIOLOGICAL INFORMATION MEASUREMENT DEVICE AND METHOD FOR CONTROLLING BIOLOGICAL INFORMATION MEASUREMENT DEVICE

PRIORITY

This is a National Stage Application under 35 U.S.C. § 365 of International Application PCT/JP2015/056845, with an international filing date of Mar. 9, 2015, which claims priority to Japanese Patent Application No. 2014-058587 filed on Mar. 20, 2014. The entire disclosures of International Application PCT/JP2015/056845 and Japanese Patent Application No. 2014-058587 are hereby incorporated herein by reference.

TECHNICAL FIELD

The present invention relates to a biological information measurement device for measuring biological information, such as a blood glucose level, from blood, for example, as well as to a method for controlling a biological information measurement device.

BACKGROUND

A conventional biological information measurement device comprised a main body case having a sensor insertion opening, a connector provided on the inside of the sensor insertion opening inside this main body case, a measurement component electrically connected to this connector, a controller connected to this measurement component, and a temperature sensor connected to this controller.

With this configuration, a biological information measurement sensor is inserted from the terminal side into the sensor insertion opening, and is electrically connected to a connector on the inside. After this, the measurement component measures the reaction current between blood and the reagent of the biological information measurement sensor, and finds the blood glucose level by correcting this measured value with temperature information from a temperature sensor.

SUMMARY

A problem encountered with the conventional art discussed above is that sometimes the measurement is not performed properly.

Specifically, with a conventional biological information measurement device, since the sensor insertion opening is open, dust or the like will sometimes come in through the sensor insertion opening. If this dust should be squeezed between the biological information measurement sensor and the connector when the former is inserted, this can result in higher contact resistance at the connector portion, which may result in improper measurement.

It is therefore an object of the present invention to perform measurement properly.

To achieve the stated object, the biological information measurement device of the present invention comprises a main body case, a connector, a measurement component, a cover, and an external temperature measurement component. The main body case has a sensor insertion opening into which a sensor is inserted. The connector is provided on the inside of the sensor insertion opening inside the main body case, and is electrically connected to the sensor inserted in the sensor insertion opening. The measurement component is electrically connected to the connector. The cover is provided on the surface of the main body case and openably and closeably covers the sensor insertion opening. The external temperature measurement component is provided on the surface of the main body case and measures the temperature of the air outside the main body case. The cover covers the external temperature measurement component along with the sensor insertion opening. This configuration achieves the desired object.

As discussed above, with the present invention, since a cover that openably and closeably covers the sensor insertion opening is provided on the surface of the main body case, when the sensor insertion opening is closed off with the cover during storage, no dust or the like can come in through the sensor insertion opening, and as a result proper measurement can be performed.

Furthermore, with the present invention, an external temperature measurement component that measures the temperature of air outside the main body case is provided on the surface of the main body case, and the cover is configured to cover the external temperature measurement component along with the sensor insertion opening.

Accordingly, when the cover is opened to make a measurement, the external temperature measurement component is opened up and exposed to the outside air. Therefore, the measured value can be corrected using the external temperature measured by the external temperature measurement component (that is, the temperature outside the main body case, or the ambient temperature of the place where the reagent is reacted with blood), and this also allows proper measurement to be performed.

DETAILED DESCRIPTION

Embodiments of the present invention will now be described through reference to the drawings.

Overview of Biological Information Measurement Device

Figure 1:
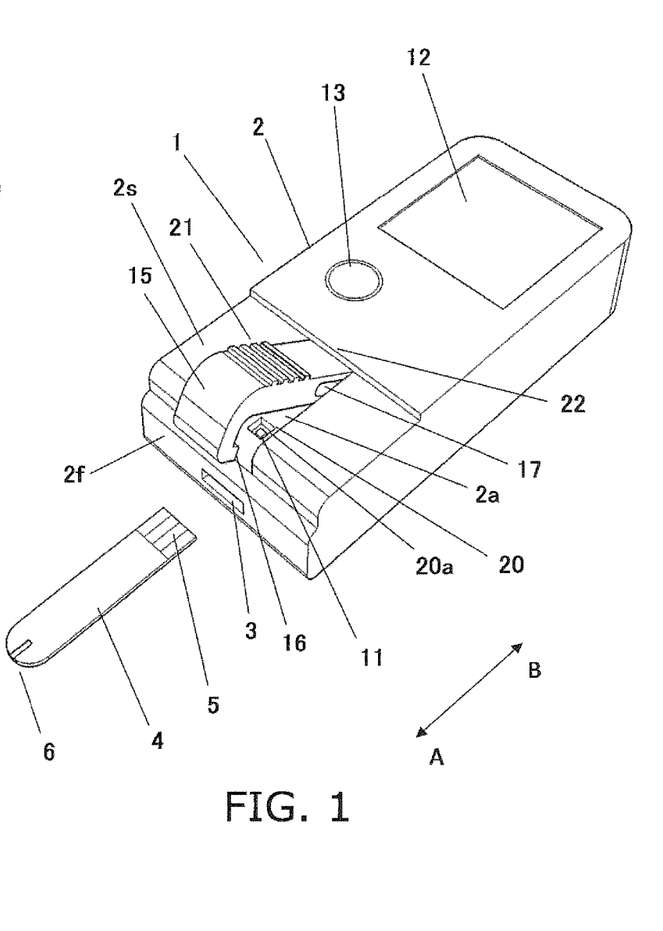
FIG. 1 is an oblique view of the biological information measurement device pertaining to an implementation of the present invention.
Figure 2:
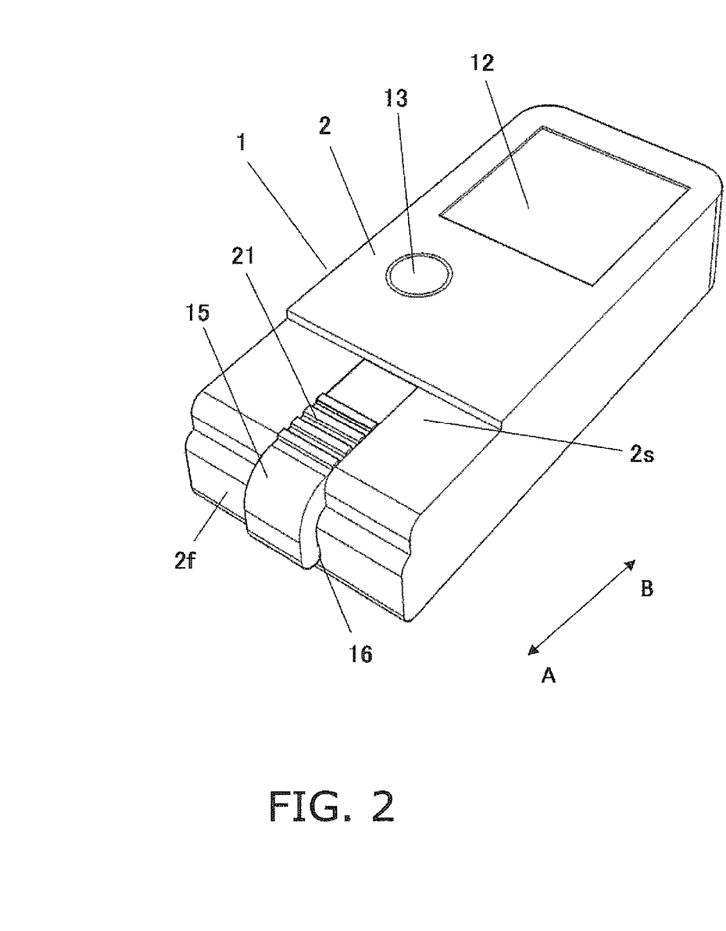
FIG. 2 is an oblique view of the biological information measurement device in FIG. 1.

FIGS. 1 and 2 show an exterior view of a biological information measurement device 1 in an embodiment of the present invention. FIG. 1 shows the state when a cover 15 (discussed below) is open, and FIG. 2 shows the state when the cover 15 is closed.

The biological information measurement device 1 in this embodiment has a main body case 2 that is cuboid in shape, a connector 8 (see FIG. 3), a measurement component 9 (see FIG. 5; discussed below), the cover 15, and an external temperature measurement component 20. A sensor insertion opening 3 is provided to the front face 2f on the front end side of this main body case 2, and a long, flat sensor 4 (an example of a biological information measurement sensor) is inserted into the sensor insertion opening 3 by being inserted from a connection terminal 5 side into the sensor insertion opening 3. When a drop of blood (an example of a biological sample) is deposited on a deposition component 6 in this inserted state, the blood glucose level of the sample is measured. In the following description, the front side refers to the sensor insertion opening 3 side, and is indicated by an arrow A. The opposite side from the arrow A is the rear side, and is indicated by an arrow B.

Also, as will be discussed in detail below, the cover 15 openably and closeably covers the sensor insertion opening 3.

Figure 3:
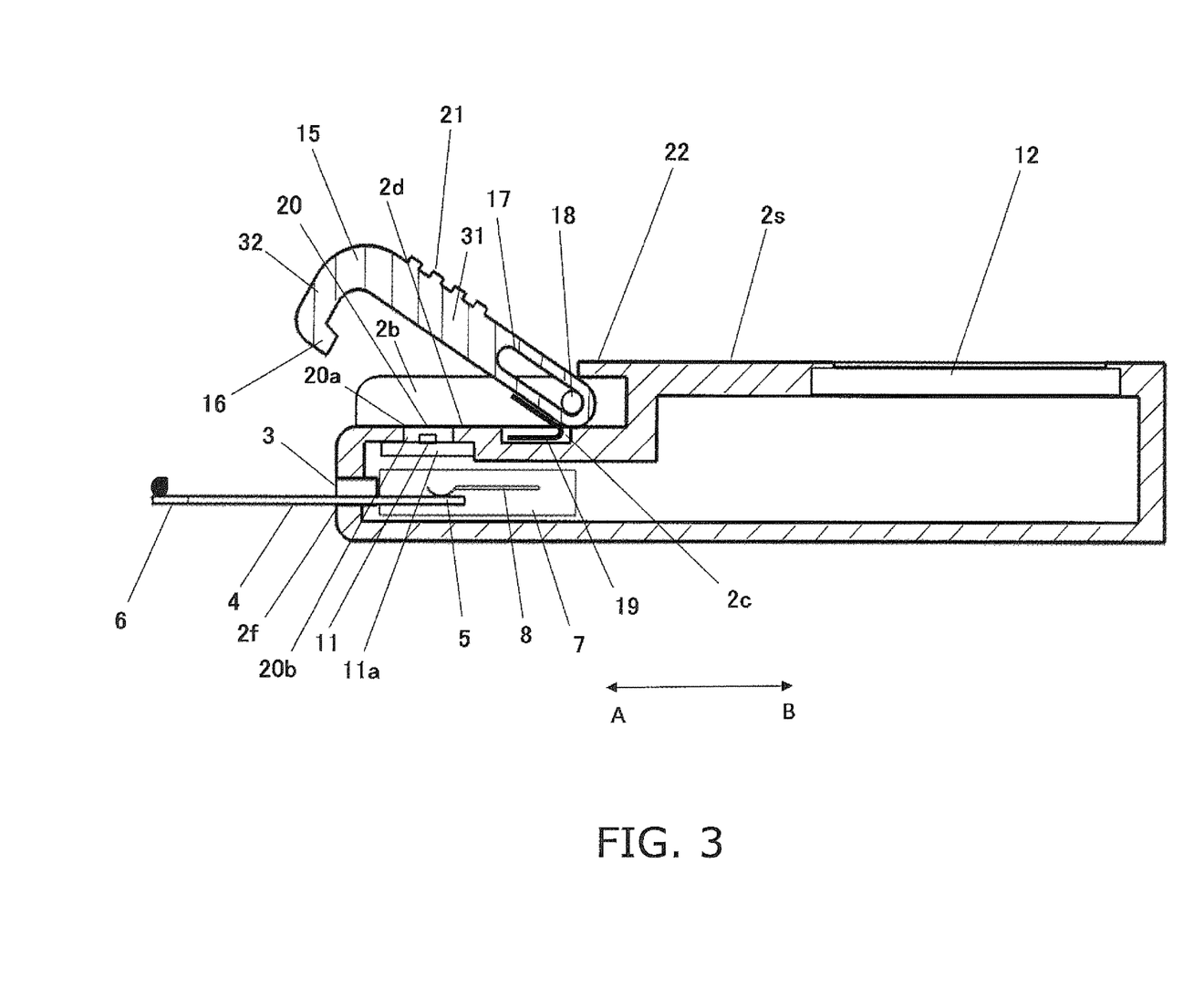
FIG. 3 is a cross section of the biological information measurement device in FIG. 1.
Figure 4:
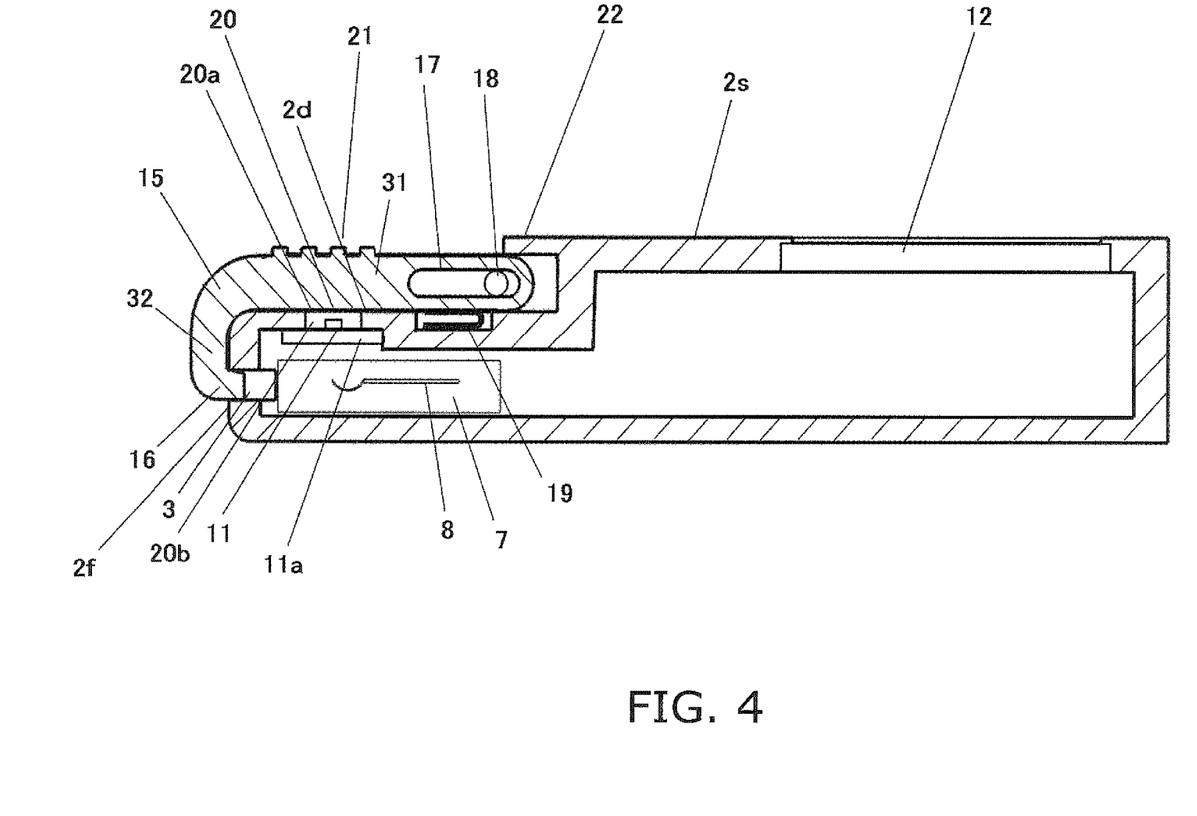
FIG. 4 is a cross section of the biological information measurement device in FIG. 1.

FIG. 3 is a cross section of the biological information measurement device 1 in a state in which the sensor 4 has been inserted. FIG. 4 is a cross section of the biological information measurement device 1 in a state in which the cover 15 is closed.

A sensor insertion component 7 is provided on the inside of the sensor insertion opening 3 in the interior of the main body case 2. When the sensor 4 is inserted through the sensor insertion opening 3 into the main body case 2, the connection terminal 5 of the sensor 4 mates with the connector 8 of the sensor insertion component 7 on the inside, and the sensor 4 is mechanically and electrically connected to the connector 8. Also, the connector 8 is electrically connected to a controller 10 (see FIG. 5).

The external temperature measurement component 20 is provided to the top face 2s of the main body case 2 (this could also be called the face on which a display component 12 is provided), and measures the outside air temperature of the biological information measurement device 1. The measurement component 9 (see FIG. 5) measures the reaction current between blood and the reagent (not shown) of the sensor 4, and calculates a blood glucose level by performing correction on the basis of the outside air temperature.

Electrical Connection of Components

Figure 5:
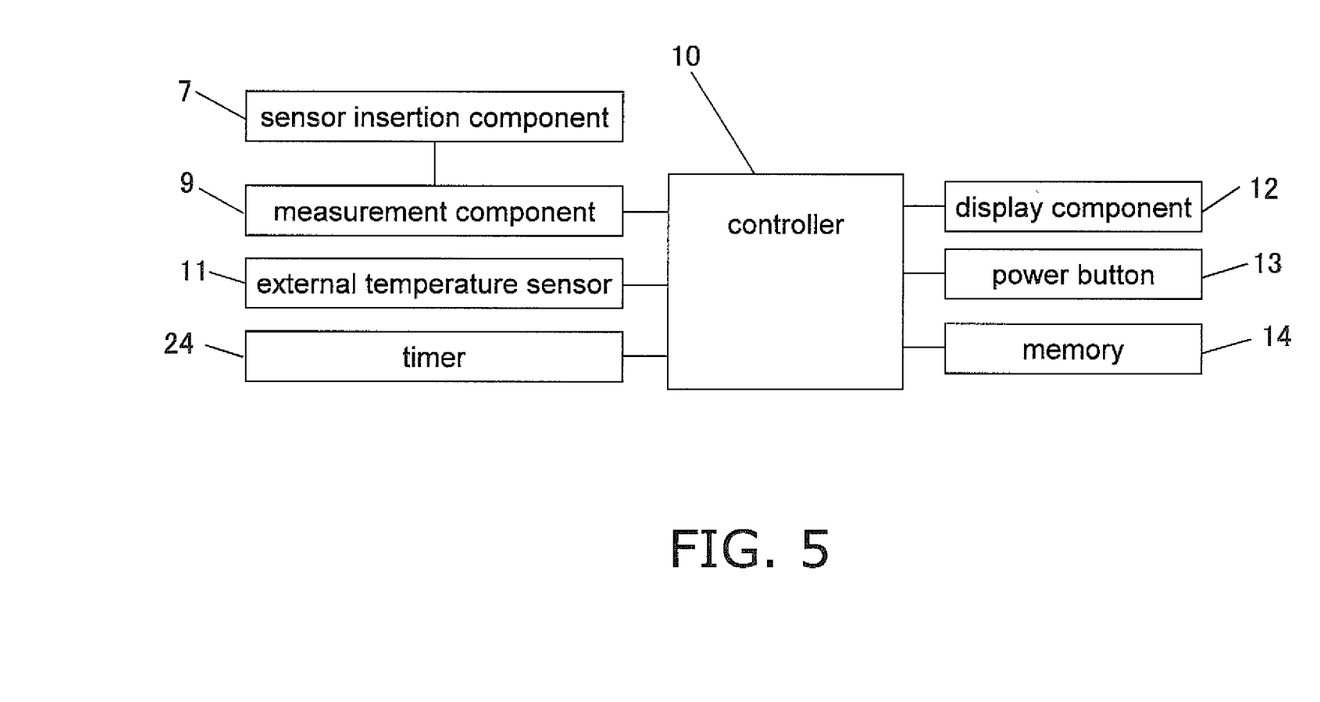
FIG. 5 is a control block diagram of the biological information measurement device in FIG. 1.

FIG. 5 shows how the various components are electrically connected.

The sensor insertion component 7 has a detecting function whereby it detects that the sensor 4 has been inserted into the sensor insertion component 7, and is electrically connected to the measurement component 9 (an example of a biological sample analyzer) that measures the biological sample. The measurement component 9 is also electrically connected to the controller 10 that controls the operation of the biological information measurement device 1.

An external temperature sensor 11 that senses the temperature of air outside the main body case 2 is electrically connected to the controller 10. Furthermore, the controller 10 is electrically connected to the display component 12, a power button 13, and a memory 14 that holds control programs and the like executed by the controller 10.

The controller 10, the measurement component 9, the memory 14 are disposed on the same control board (not shown), and are held inside the main body case 2.

The controller 10 performs control over the operation of the components shown in FIG. 5, and its programs are stored in the memory 14. The controller 10, the measurement component 9, and the memory 14 are each constituted by an electrical circuit.

In the measurement of a blood glucose level, the user pushes the power button 13 to activate the biological information measurement device 1, and sticks the sensor 4 into the connector 8 of the sensor insertion component 7. After this, blood is deposited on the deposition component 6 of the sensor 4 in FIG. 1, whereupon the reaction current between the blood and the reagent (not shown) of the sensor 4 is measured by the measurement component 9. The controller 10 finds the blood glucose level by correcting this measured value with the temperature sensed by the external temperature sensor 11, and this value is displayed on the display component 12.

The display component 12 is provided to the rear end of the top face 2s of the main body case 2, and the power button 13 is provided on the front side of the display component 12.

Cover

As shown in FIGS. 1 and 2, in this embodiment, the cover 15, which has a long, flat shape and openably and closeably covers the sensor insertion opening 3 on the front end side, is provided on the upper face at the outer surface of the main body case 2.

As shown in FIG. 3, a sealing component 16 that seals off the sensor insertion opening 3 is formed in the cover 15 by bending back the front end side of the cover downward in a hook shape.

As shown in FIG. 1, a disposition component 2a on which the cover 15 is disposed is formed in the front center of the top face 2s of the main body case 2. The disposition component 2a is formed in the shape of a groove running in the longitudinal direction. In FIG. 3, the cover 15 is made up of a first portion 31 formed in the longitudinal direction, a second portion 32 that is formed downward from the front end of the first portion 31, and the above-mentioned sealing component 16. The sealing component 16 is formed toward the rear side from the lower end of the second portion 32.

A slot 17 that passes through in a direction perpendicular to the longitudinal direction of the cover 15 (also called the width direction) is provided on the rear end side of the cover 15 (the rear end of the first portion 31). A pin 18 that goes into this slot 17 is attached to the main body case 2. The two ends of the pin 18 are fixed to opposing wall faces 2b of the disposition component 2a (see FIG. 3).

When this slot 17 engages with the pin 18, the cover 15 is attached to the top face 2s of the main body case 2 in a state of being able to slide in the longitudinal direction of the main body case 2. Also, the cover 15 is configured to be rotatable above the main body case 2, with the pin 18 as the axis of rotation, as shown in FIGS. 3 and 4.

A leaf spring 19 (an example of a biasing member) that biases the cover 15 upward is provided between the cover 15 and the main body case 2. A recess 2c is formed in the bottom of the disposition component 2a, ahead of the pin 18, and the leaf spring 19 is disposed in this recess 2c.

A textured finger placement part 21 is formed on the upper face of the first portion 31 of the cover 15. This finger placement part 21 is provided to make it easier for the user to slide and rotate the cover 15.

When the biological information measurement device 1 is put away, the cover 15 is rotated from the state in FIG. 1 to the main body case 2 side, so that its sealing component 16 is opposite the sensor insertion opening 3. The cover 15 is then slid to the rear so as to push the sealing component 16 into the sensor insertion opening 3, which closes off the sensor insertion opening 3 with the cover 15 as shown in FIGS. 2 and 4. In a state in which the sealing component 16 is mated with the sensor insertion opening 3, the first portion 31 of the cover 15 fits into the disposition component 2a, and the second portion 32 is located ahead of the front face 2f.

In this embodiment, since the cover 15 is provided to the main body case 2 so as to openably and closeably cover the sensor insertion opening 3, when the device is put away, dust and the like are prevented from coming in through the sensor insertion opening 3. Therefore, dust can be prevented from being squeezed against the connector 8 as the sensor 4 is inserted, and this prevents an increase in contact resistance at the connector 8 portion during use.

The result of this is that proper measurement can be performed.

External Temperature Measurement Component

In measurement, the reaction between blood and the reagent of the sensor 4 is converted into an electrical signal and measured, and this measured value is corrected with the ambient temperature of the reaction to find a blood glucose level, but the correction is preferably carried out at the temperature of the place where the reagent and the blood are reacted. That is, the correction is preferably done at the temperature outside the main body case 2.

In view of this, with the biological information measurement device 1 in this embodiment, as shown in FIG. 1, a configuration is used in which the external temperature measurement component 20, which measures the temperature of the air outside the main body case 2, is provided to the outer surface (in FIG. 1, the top face 2s) of the main body case 2, and the cover 15 covers the external temperature measurement component 20 along with the sensor insertion opening 3.

Accordingly, when the cover 15 is opened for measurement, the external temperature measurement component 20 is opened up along with the sensor insertion opening 3 and exposed to the outside air. Therefore, the measured value can be corrected using the external temperature measured by this external temperature measurement component 20 (that is, the ambient temperature of the place where the reagent and blood are reacted, which is the temperature outside the main body case).

This will be described in specific terms below.

As shown in FIGS. 3 and 4, in this embodiment an external temperature measurement opening 20a is provided at the portion opposite the lower face side of the cover 15, which is the portion covered along with the sensor insertion opening 3 by the cover 15 (could also be called the bottom 2d of the disposition component 2a).

The inside of the external temperature measurement opening 20a (the lower side in FIG. 3) is formed as a cylindrical space 20b (an example of a measurement space) that reaches into the interior of the main body case 2, and the external temperature sensor 11 is disposed on the inside of this cylindrical space 20b. That is, in this embodiment, the external temperature measurement component 20 has the external temperature measurement opening 20a provided on the surface of the main body case 2, the cylindrical space 20b, and the external temperature sensor 11. The external temperature sensor 11 is mounted on a substrate 11a provided in the interior of the main body case 2.

The cover 15 is configured to open and close the sensor insertion opening 3 and the external temperature measurement component 20 simultaneously. Specifically, since the cover 15 is hook-shaped and is formed from the top face 2s all the way to the front face 2f, the portion of the top face 2s to which the external temperature measurement component 20 is provided (the bottom 2d of the disposition component 2a) can be opened or closed simultaneously with the portion of the front face 2f to which the sensor insertion opening 3 is provided.

Accordingly, when the biological information measurement device 1 is put away, as shown in FIG. 4, when the sensor insertion opening 3 is closed by the cover 15, the external temperature measurement opening 20a of the external temperature measurement component 20 is also closed, and the external temperature sensor 11 on the inside is blocked off from the outside air. This prevents dust and so forth from coming into the external temperature measurement opening 20a, and also prevents the external temperature sensor 11 of the external temperature measurement component 20 from being soiled when touched by the user's fingers.

During measurement, when the user places a finger on the finger placement part 21 provided to the upper face of the cover 15 and slides it forward, the sealing component 16 is pulled out of the sensor insertion opening 3. After this, when the finger is removed from the finger placement part 21, as shown in FIG. 1, the cover 15 is rotated upward by the leaf spring 19, and the sensor insertion opening 3 is opened up.

At the same time, then external temperature measurement opening 20a of the external temperature measurement component 20 is opened, and the external temperature sensor 11 on the inside is exposed to the outside air.

As a result, during measurement, the measured value can be corrected using the external temperature measured by this external temperature sensor 11 (that is, the ambient temperature of the place where the reagent of the sensor 4 and blood are reacted, which is the temperature outside the main body case 2). This also allows proper measurement to be performed.

Let us describe this state by giving an example. For instance, let us assume that the user is about to eat on a summer day, and has moved his biological information measurement device 1 from his own cool, air-conditioned room into the hot kitchen, and that he has measured his blood glucose level before the meal. In this case, the biological information measurement device 1 is moved from a cool place to a hot place.

With a conventional biological information measurement device, the temperature sensor is provided in the interior of the device, and this temperature sensor measures the temperature in the interior of the biological information measurement device. In this case, the internal temperature of the biological information measurement device that had been in a cool room rises, but it can take from a few minutes to about 20 minutes, for example, until it matches the external temperature of the hot kitchen. Therefore, if measurement is performed while the internal temperature of the biological information measurement device is still rising to match the temperature of the kitchen, the temperature sensor of the biological information measurement device will not be able to sense the kitchen temperature accurately.

In contrast, with the biological information measurement device 1 in this embodiment, when the cover 15 is opened for measurement, as discussed above, the sensor insertion opening 3 is opened up and the external temperature sensor 11 of the external temperature measurement component 20 is also exposed to the outside air. Therefore, the temperature of the kitchen (that is, the temperature outside the main body case 2) can be sensed by the exposed external temperature sensor 11, so the kitchen temperature can be sensed quickly and accurately.

As shown in FIGS. 3 and 4, the external temperature sensor 11 is mounted on the substrate 11a, which is dedicated for use with the external temperature sensor 11, and the substrate 11a is separate from the control board (not shown) on which the controller 10 is mounted. That is, the configuration is such that the external temperature sensor 11 and the control board on which the controller 10 is mounted are thermally isolated. Specifically, the controller 10 generates heat as it performs its various controls, and the control board holds this heat, but since the external temperature sensor 11 is thermally isolated from the control board, the external temperature can be properly sensed.

If the substrate 11a of the external temperature sensor 11 consists of a film substrate, then the substrate can be very thin. Therefore, the film substrate can be rapidly acclimatized to the external temperature, and the external temperature sensor 11 will be able to sense the external temperature quickly.

Furthermore, in this embodiment, the external temperature measurement opening 20a of the external temperature measurement component 20 and the sensor insertion opening 3 are disposed at different locations, apart from each other, on the surface of the main body case 2.

More precisely, the sensor insertion opening 3 is provided to the front face 2f of the main body case 2, and the external temperature measurement opening 20a constituting the external temperature measurement component 20 is provided to the top face 2s. That is, the sensor insertion opening 3 and the external temperature measurement opening 20a are disposed apart from each other on different faces on the outer surface of the main body case 2.

Therefore, as shown in FIG. 3, even in a state in which the sensor 4 has been inserted into the sensor insertion opening 3, the external temperature sensor 11 will be exposed to the outside air through the external temperature measurement opening 20a, which is provided separately from the sensor insertion opening 3, so the external temperature can be properly measured. Also, when the sensor 4 is inserted into the sensor insertion opening 3 on the front face side, this configuration prevents accidental touching of the external temperature measurement component 20 that could soil the external temperature measurement component 20.

Stopper

A stopper 22 that stops the upward rotation of the cover 15 at a specific location is further provided to the main body case 2 in this embodiment. When the cover 15 is rotated upward and the external temperature measurement opening 20a of the external temperature measurement component 20 and the sensor insertion opening 3 have been opened up, the stopper 22 stops the cover 15 in a state of being opposite the external temperature measurement opening 20a at a specific gap.

The stopper 22 is a flat member, and is formed to stick out forward from the upper end on the rear side of the groove-shaped disposition component 2a. The stopper 22 is disposed on the upper side of the pin 18, hits the cover 15 when the cover 15 is rotated upward, and restricts any further rotation of the cover 15.

Therefore, when the sensor insertion opening 3 has been opened up, the upward rotation of the cover 15 is restricted by the stopper 22. As can be seen from FIG. 1, the external temperature sensor 11 and the external temperature measurement opening 20a on the lower side are protected by this cover 15. Therefore, the external temperature sensor 11 will not be touched by the user, and as a result will be able to sense the external temperature without being affected by the body temperature of the user. This again allows the biological information measurement device 1 in this embodiment to perform measurement properly.

As described above, when the cover 15 is opened, the external temperature measurement component 20 is exposed to the outside air, so the external temperature sensor 11 of the external temperature measurement component 20 can sense the external temperature directly. Accordingly, the external temperature sensor 11 reacts well to the external temperature, and when it has been moved from a cool room into a hot room, for example, it is able to sense the external temperature in that environment quickly. That is, there is no need to wait from a few minutes to 20 minutes until the temperatures match inside and outside the main body case 2 as in the past, and the measurement can be performed rapidly.

Main Features (1)

The biological information measurement device 1 in this embodiment comprises the main body case 2, the connector 8, the measurement component 9, the cover 15, and the external temperature measurement component 20. The main body case has the sensor insertion opening 3 into which the sensor 4 (an example of a biological information measurement sensor) is inserted. The connector 8 is provided on the inside of the sensor insertion opening 3 inside the main body case 2. The connector 8 is electrically connected to the sensor 4 inserted in the sensor insertion opening 3. The measurement component 9 is electrically connected to the connector. The cover 15 is provided on the surface of the main body case 2 and openably and closeably covers the sensor insertion opening 3. The external temperature measurement component 20 is provided on the surface of the main body case 2 and measures the temperature of the air outside the main body case 2. The cover 15 covers the external temperature measurement component 20 along with the sensor insertion opening 3.

Thus, since the cover 15 is provided to openably and closeably cover the sensor insertion opening 3, when the sensor insertion opening 3 is closed off by the cover 15 when the device is put away, no dust or the like can come in through the sensor insertion opening 3, and as a result the proper measurement can be performed.

Furthermore, the external temperature measurement component 20, which measures the temperature of the air outside the main body case 2, is provided on the surface of the main body case 2, and the cover 15 is configured to cover the external temperature measurement component 20 along with the sensor insertion opening 3.

Accordingly, when the cover 15 is opened for measurement, the external temperature measurement component 20 is opened up and exposed to the outside air. Therefore, the measured value can be corrected using the external temperature measured by this external temperature measurement component 20 (that is, the ambient temperature of the place where the reagent and blood are reacted, which is the temperature outside the main body case), which again allows the proper measurement to be performed.

(2)

With the biological information measurement device 1 in this embodiment, the opening and closing of the sensor insertion opening 3 and the external temperature measurement component 20 are performed simultaneously.

Thus opening and closing the sensor insertion opening 3 simultaneously with the external temperature measurement component 20 allows the external temperature of the main body case 2 to be measured when the sensor 4 is inserted in the sensor insertion opening 3 for measurement. Therefore, the user will not forget to expose the external temperature measurement component 20 to the outside air at the time of measurement, and the external temperature can be properly measured, which means that proper measurement can be carried out.

(3)

With the biological information measurement device 1 in this embodiment, the sensor insertion opening 3 and the external temperature measurement component 20 are provided at different locations on the surface of the main body case 2. The sensor insertion opening 3 is provided on the front face 2*f*, and the external temperature measurement component 20 is provided on the top face 2*s*.

Even in a state in which the sensor 4 has been inserted into the sensor insertion opening 3, the external temperature sensor 11 will be exposed to the outside air through the external temperature measurement opening 20*a* provided separately from the sensor insertion opening 3, so the external temperature can be measured properly. Also, when the sensor 4 is inserted into the sensor insertion opening 3 on the front face side, the user will be less likely to accidentally touch the external temperature measurement component 20 and soil the external temperature measurement component 20.

(4)

With the biological information measurement device 1 in this embodiment, the external temperature measurement component 20 has the external temperature measurement opening 20*a* and the external temperature sensor 11. The external temperature measurement opening 20*a* is provided to the surface of the main body case 2. The external temperature sensor 11 is provided on the inside of the external temperature measurement opening 20*a*.

This allows the external temperature sensor 11 to be exposed to the outside air, and makes it less likely that the user will touch it with a finger.

(5)

With the biological information measurement device 1 in this embodiment, the cover 15 blocks off the external temperature measurement opening 20*a* in a state in which the sensor insertion opening 3 has been closed, and blocks the external temperature sensor 11 from the outside air. Consequently, this makes it less likely that dust and the like will come in through the external temperature measurement opening 20*a*, and also makes it less likely that the external temperature sensor 11 of the external temperature measurement component 20 will be touched with a finger and soiled.

(6)

With the biological information measurement device 1 in this embodiment, the sealing component 16 that covers the sensor insertion opening 3 is formed on the front end side of the cover 15. The cover 15 is linked to the main body case 2 slidably with respect to the surface of the main body case 2. This allows the sealing component 16 to be inserted into the sensor insertion opening 3, and the sensor insertion opening 3 to be closed.

(7)

With the biological information measurement device 1 in this embodiment, the cover 15 is provided rotatably with respect to the main body case 2. The main body case 2 has the stopper 22, which stops the cover 15 in a state of being opposite the external temperature measurement component 20 at a specific gap. The external temperature measurement component 20 on the lower side is protected by this cover 15. Therefore, the external temperature sensor 11 will not be touched by the user, and as a result will be able to sense the external temperature without being affected by the body temperature of the user.

Next, the biological information measurement device 1 in an implementation pertaining to the present invention will be described. The biological information measurement device 1 in an implementation involves a modification to the measurement operation of the biological information measurement device 1 in an above-describe implementation, and even better measurement is performed by taking advantage of the fact that the external temperature can be sensed quickly.

That is, when the measurement site (the measurement environment) is changed, with a conventional biological information measurement device it takes time for the temperatures inside and outside the main body case 2 to match up. If measurement is performed before the temperatures match up, the proper external temperature cannot be measured, and as a result proper measurement cannot be performed.

In view of this, with the biological information measurement device 1 in this embodiment, the controller 10 determines whether or not the temperature sensed by the external temperature sensor 11 is changing before measurement with the measurement component 9, and if it is determined that the sensed temperature is changing, a period is provided during which measurement with the measurement component 9 is not possible.

Therefore, if the controller 10 determines that the temperature sensed by the external temperature sensor 11 is changing, it is concluded that the measurement environment has changed, and that the external temperature in this measurement environment has not been acquired. Measurement with the measurement component 9 then moves into the measurement-impossible period in which measurement with the measurement component 9 is not possible. After this, once the change in the sensed temperature of the external temperature sensor 11 is sufficiently small, at that point the external temperature of the measurement environment is determined to have been acquired, the measurement-impossible period is ended, and measurement is performed.

Specifically, switching to the measurement-impossible period when the sensed temperature of the external temperature sensor 11 is changing means that no measurement will be performed at a sensed temperature that is in the midst of changing. As a result, measurement is delayed until the proper external temperature is sensed, and this allows better measurement to be performed.

It might seem that providing this measurement-impossible period would make the device more inconvenient to use, but in this embodiment, as discussed above, the external temperature measurement component 20 is provided to the outer surface of the main body case 2, and the configuration is such that the external temperature measurement component 20 is exposed to the outside air during measurement. Therefore, there is better conformity with the external temperature, so the measurement-impossible period can be concluded while the user is making preparations for measurement, such as pricking a finger to draw blood. Accordingly, there is substantially no inconvenience.

Configuration of Controller

The configuration of the controller 10 of the biological information measurement device 1 in an implementation will now be described.

Figure 6:
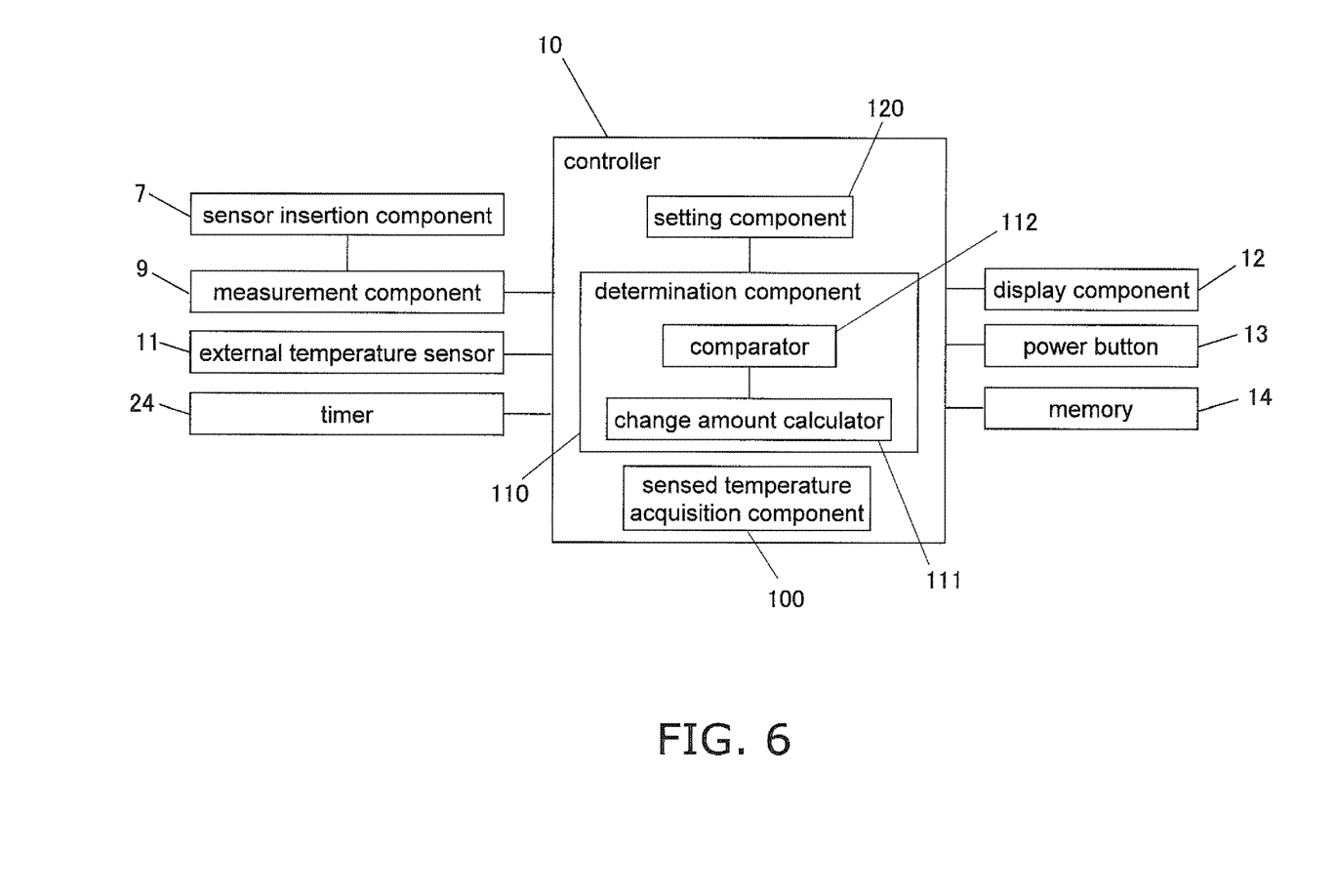
FIG. 6 is a block diagram of the control configuration of the biological information measurement device pertaining to an implementation of the present invention.

FIG. 6 illustrates the configuration of the controller 10 in this embodiment. The controller 10 has a sensed temperature acquisition component 100, a determination component 110, and a setting component 120.

The sensed temperature acquisition component 100 acquires the external temperature sensed by the external temperature sensor 11.

The determination component 110 determines whether or not the temperature acquired by the sensed temperature acquisition component 100 is changing. More precisely, the determination component 110 has a change amount calculator 111 and a comparator 112. The change amount calculator 111 calculates the amount of temperature change per unit of time from a plurality of sensed temperatures sensed by the external temperature sensor 11. The comparator 112 compares the temperature change amount calculated by the change amount calculator 111 with the permissible change amount, and determines whether or not the sensed temperature is changing.

If the temperature change amount found by the comparator 112 exceeds the permissible change amount, the setting component 120 performs the setting so that measurement with the measurement component 9 cannot be executed, and causes the display component 12 to display a message to the effect that measurement is impossible. If the comparator 112 determines that the temperature change amount is within the permissible range, the setting component 120 cancels the state in which measurement is impossible.

Control Operation

This operation will be described in specific terms through reference to the flowchart in FIG. 7.

Figure 7:
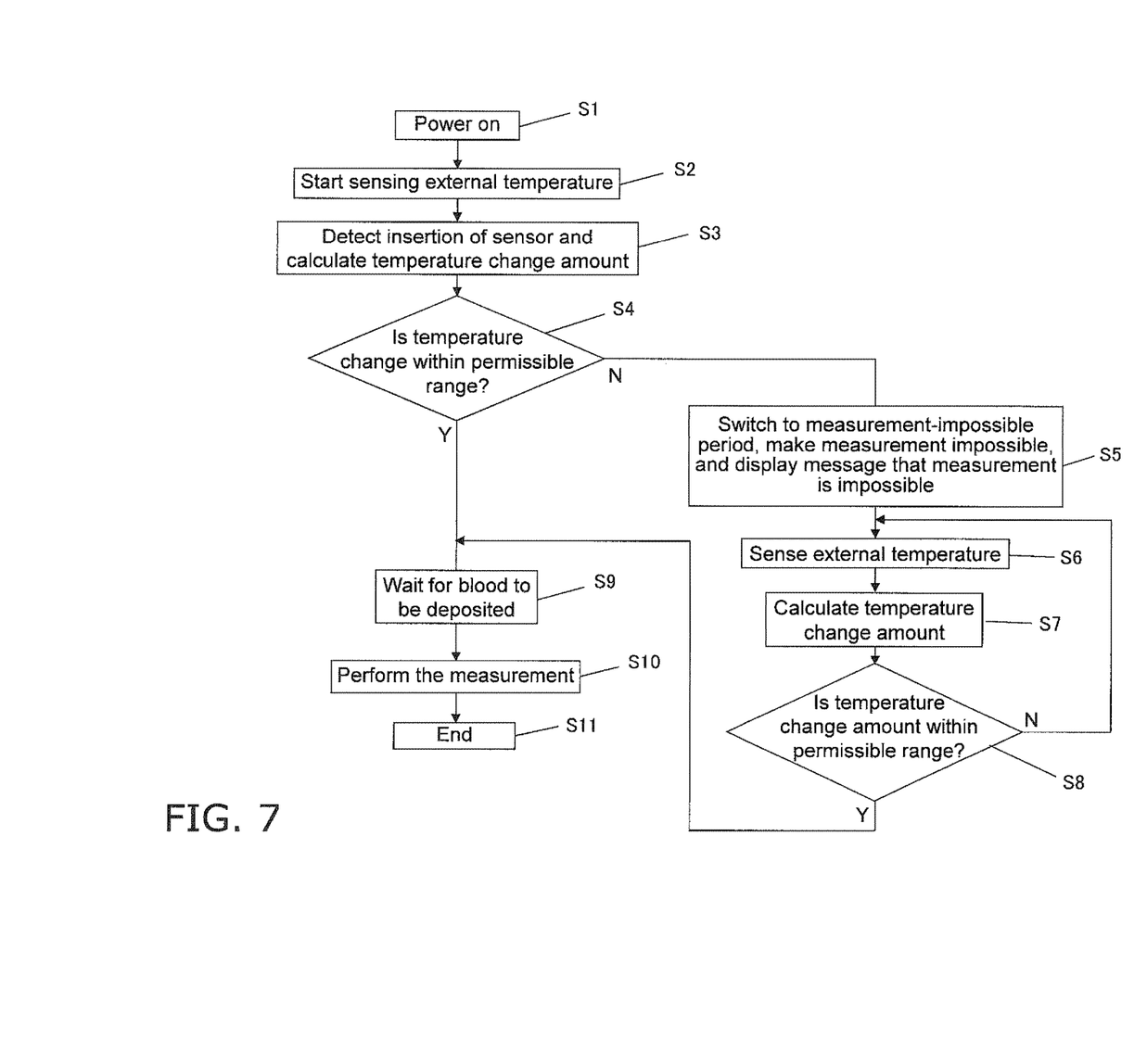
FIG. 7 is a flowchart of the control operation of the biological information measurement device pertaining to an implementation of the present invention.

When the user pushes the power button 13 to switch on the power (S1 in FIG. 7), the sensed temperature acquisition component 100 of the controller 10 actuates a timer 24 (FIG. 5) that is electrically connected to the controller 10, and uses the external temperature sensor 11 to sense the external temperature at regular time intervals (such as every three seconds) (S2 in FIG. 7).

After this, when the user inserts the sensor 4 into the main body case 2, the sensor insertion component 7 detects that the sensor 4 has been inserted into the sensor insertion component 7. At this point the change amount calculator 111 calculates the temperature change amount per unit of time (such as one minute) from a plurality of sensed temperatures sensed every three seconds by the external temperature sensor 11 (S3 in FIG. 7). This S3 corresponds to an example of a change amount calculation step.

The determination component 110 then determines whether or not the temperature sensed by the external temperature sensor 11 is changing. More specifically, it determines whether or not the calculated temperature change amount is within a permissible range (such as 1° C./minute or less) (S4 in FIG. 7). This S4 corresponds to an example of a comparison step. S3 and S4 in FIG. 7 correspond to an example of a determination step.

This permissible range is provided to determine whether or not the temperature sensed by the external temperature sensor 11 is changing, and is stored ahead of time in the memory 14. The comparator 112 compares the calculated temperature change amount with the permissible range. If the calculated temperature change amount is within the permissible range, it is determined that the temperature sensed by the external temperature sensor 11 is stable, that is, that the external temperature was accurately sensed by the external temperature sensor 11.

It may also be configured that the change amount calculator 111 finds the temperature change amount as an absolute value and the comparator compare this absolute value with a reference value for determining whether or not the temperature sensed by the external temperature sensor 11 is changing.

When the temperature change amount is outside the permissible range, since the temperature change amount is large, the determination component 110 determines that the measurement environment has changed, and that an accurate external temperature has not been acquired in this measurement environment. At this point the setting component 120 provides a measurement-impossible period, and switches over to this measurement-impossible period (S5 in FIG. 7). This S5 corresponds to an example of the setting step.

When a state switches to the measurement-impossible period (S5 to S8 in FIG. 7), the setting component 120 makes measurement with the measurement component 9 impossible, since no external temperature has been acquired in this measurement environment. The setting component 120 then causes the display component 12 to display a message to the effect that the measurement environment has changed, and a message to the effect that measurement is impossible. For example, a message of "Measurement environment has changed. Preparing for measurement. Please wait" is displayed.

In this measurement-impossible period, the controller 10 repeats S6 to S8 in FIG. 7 until the amount of change in the external temperature is within the permissible range. Specifically, the sensed temperature acquisition component 100 acquires the external temperature sensed by the external temperature sensor 11 every three seconds (S6 in FIG. 7), and the change amount calculator 111 calculates the amount of change in the sensed external temperature by the same processing as in S3 in FIG. 7 (S7 in FIG. 7). The comparator 112 then confirms whether or not the temperature change amount calculated in S7 is within the permissible range, by the same processing as in S4 in FIG. 7 (S8 in FIG. 7). The control processing of S6 to S8 is repeated.

If the temperature change amount is within the permissible range, since the temperature change amount is sufficiently small, the determination component 110 determines that the temperature sensed by the external temperature sensor 11 has stabilized. That is, it is determined by the determination component 110 that an accurate external temperature has been acquired, and the setting component 120 ends the measurement-impossible period. Accordingly, the setting component 120 causes the display component 12 to display a message indicating that measurement is possible, and prompting the user to deposit blood. For instance, "Measurement preparations complete. Deposit blood now." is displayed.

The controller 10 then waits for blood to be deposited (S9 in FIG. 7).

In S4 in FIG. 7, if the calculated temperature change amount is within the permissible range, it is determined that the temperature sensed by the external temperature sensor 11 has stabilized, that is, that an accurate external temperature has been sensed. The processing then moves on to S9 in FIG. 7, and the controller 10 waits for blood to be deposited.

Once the patient deposits blood on the deposition component 6 of the sensor 4 shown in FIG. 1, the measurement component 9 performs its measurement. This measurement is carried out according to an ordinary procedure, just as in the measurement described above. That is, the reaction current between the blood and the reagent (not shown) of the sensor 4 is measured, and the controller 10 corrects this measured value with the temperature sensed by the external temperature sensor 11 to find the blood glucose level (S10 in FIG. 7).

Once this value is displayed on the display component 12, the measurement is ended (S11 in FIG. 7).

Specifically, in this embodiment, before measurement a measurement-impossible period is imposed when a state in which the measurement environment has changed is detected, and this postpones the measurement until the proper external temperature is sensed.

Therefore, since the measurement is performed after the correct external temperature has been sensed, the proper measurement can be carried out.

A measurement performance temperature range (such as from −5° C. to 40° C.) is set as the temperature at which a biological sample can be measured in the biological information measurement device 1. If the external temperature sensor 11 senses a temperature outside this measurement performance temperature range, it is concluded that the biological sample cannot be measured accurately, and the controller 10 displays a measurement error. Confirmation of the temperature change amount prior to measurement is performed within the measurement performance temperature range (such as from −5° C. to 40° C.), and is performed in order to sense the correct external temperature within this measurement performance temperature.

Specifically, in S2 in FIG. 7 sensing of the external temperature is begun, and if the external temperature is outside the range of −5° C. to 40° C., the controller 10 causes the display component 12 to give an error display.

Also, while the controller 10 is waiting for blood to be deposited in S9 in FIG. 7, the sensed temperature acquisition component 100 may acquire the sensed external temperature, the change amount calculator 111 may calculate the temperature change amount, and the comparator 112 may confirm whether or not the temperature change amount is within the permissible range. If the temperature change amount is not within the permissible range, the setting component 120 may impose a measurement-impossible period, switch to this measurement-impossible period, and perform control to carry out the processing of S5 to S8 in FIG. 7.

As a result of this control, the state switches to the measurement-impossible period if it is detected that the measurement environment has changed while the controller 10 is waiting for blood to be deposited, so the measurement can be postponed until the external temperature is sensed in this measurement environment.

Accordingly, since measurement is carried out after the correct external temperature has been sensed, the proper measurement can be performed.

Main Features

In addition, certain implementations may have some or all of the following features.

(1)

The biological information measurement device 1 in this embodiment comprises the determination component 110 and the setting component 120. The determination component 110 determines whether or not the temperature sensed by the external temperature measurement component 20 is changing, prior to measurement by the measurement component 9. If it is determined that the sensed temperature is changing, the setting component 120 imposes a measurement-impossible period in which measurement by the measurement component 9 is impossible.

Thus making measurement impossible when the sensed temperature is changing makes it less likely that the measured value will be incorrect.

(2)

With the biological information measurement device 1 in this embodiment, the determination component 110 has the change amount calculator 111 and the comparator 112. The change amount calculator 111 calculates the amount of temperature change per unit of time from a plurality of sensed temperatures sensed by the external temperature measurement component 20. The comparator 112 compares the calculated temperature change amount with a reference value for determining whether or not the temperature sensed by the external temperature measurement component 20 is changing, and thereby determines whether or not the sensed temperature is changing.

This makes it possible to determine whether or not the sensed temperature is changing.

(3)

With the biological information measurement device 1 in this embodiment, the setting component 120 enables measurement by the measurement component 9 when the comparator 112 has determined that the sensed temperature is not changing.

Consequently, when the device is moved to a place where the temperature is different, measurement can be performed after the measured value produced by the external temperature measurement component 20 has stabilized. Therefore, when subjecting the measured value to temperature correction, the correction can be performed with the proper temperature, and the proper measurement can be carried out.

(4)

With the biological information measurement device 1 in this embodiment, the setting component 120 is connected to the display component 12. The setting component 120 causes the display component 12 to display a message to the effect that measurement is impossible during the measurement-impossible period. This allows the user to confirm that measurement cannot be done right now.

(5)

With the biological information measurement device 1 in this embodiment, the determination component 110 sets a temperature range at which the measurement component 9 performs its measurement, and determines whether or not the temperature sensed by the temperature sensor is changing, within this temperature range. This makes it possible to determine whether or not the sensed temperature is changing.

(6)

The method for controlling the biological information measurement device in this embodiment is a method for controlling a biological information measurement device comprising the main body case 2, the connector 8, the cover 15, and the external temperature measurement component 20, said method comprising S3 and S4 (an example of determination steps) and S5 (impossible period setting step). The main body case 2 has the sensor insertion opening 3 in which the sensor 4 (an example of a biological information measurement sensor) is inserted. The connector 8 is provided on the inside of the sensor insertion opening 3 inside the main body case 2. The connector 8 is electrically connected to the sensor 4 inserted into the sensor insertion opening 3. The cover 15 is provided to the surface of the main body case 2, and openably and closeably covers the sensor insertion opening 3. The external temperature measurement component 20 is provided to the surface of the main body case 2, and measures the temperature of the air outside the main body case 2. The cover 15 covers the external temperature measurement component 20 along with the sensor insertion opening 3.

S4 (an example of a determination step) involves determining whether or not the temperature sensed by the external temperature measurement component 20 is changing, prior to measurement by the measurement component 9. S5

(an example of a setting step) involves imposing a measurement-impossible period, in which measurement with the measurement component 9 is impossible, when it has been determined that the sensed temperature is changing.

Thus making measurement impossible when the sensed temperature is changing makes it less likely that the measured value will be incorrect.

Other Embodiments (A)

Figure 8:
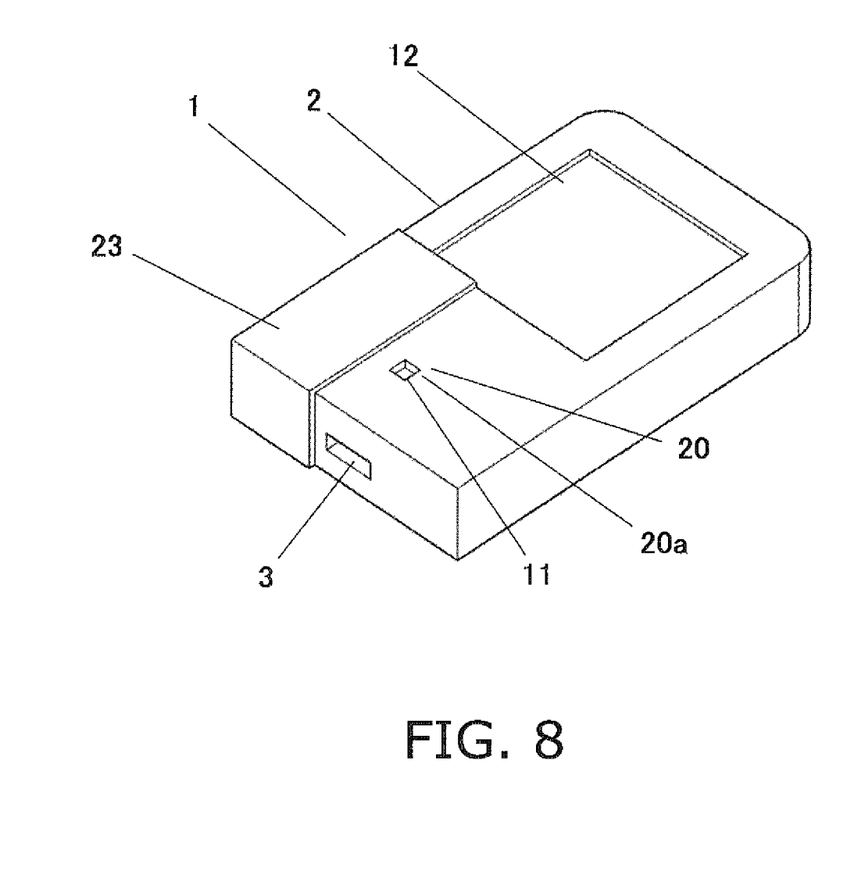
FIG. 8 is an oblique view of the biological information measurement device in a modification example of an embodiment pertaining to the present invention.

In certain implementations above, the cover 15, which is fixed on the rear end side and rotated in the up and down direction, is provided to cover the sensor insertion opening 3 and the external temperature measurement component 20, but as shown in FIG. 8, a slide cover 23 may be provided to the surface of the main body case 2.

Specifically, a configuration may be used in which the slide cover 23 is slidably provided to the surface of the main body case 2, and this slide cover 23 opens and closes the external temperature measurement component 20 along with the sensor insertion opening 3.

With this configuration, when the sensor insertion opening 3 is closed with the slide cover 23 when the device is put away, no dust or the like will come in through the sensor insertion opening 3, and as a result the proper measurement can be performed.

Also, when the cover is opened at the time of measurement to open up the sensor insertion opening 3, the external temperature measurement opening 20a constituting the external temperature measurement component 20 is opened up, and the external temperature sensor 11 is exposed to the outside air. Therefore, the measured value can be corrected using the external temperature measured by the external temperature measurement component 20 (that is, the ambient temperature of the place where the reagent and blood are reacted, which is the temperature outside the main body case 2), and proper measurement can be performed.

(B)

In certain implementations above, the configuration was such that the sensor 4 was inserted into the sensor insertion opening 3 from the connection terminal 5 side, but the configuration may instead be such that a plurality of sensors 4 are built into the main body case 2, and the deposition component 6 of a sensor 4 is thrust outside the main body case 2 from inside the main body case 2 for a sensor 4 to be inserted into the sensor insertion opening 3.

INDUSTRIAL APPLICABILITY

The biological information measurement device and the method for controlling a biological information measurement device of the present invention have the effect of allowing the proper measurement to be performed, and are expected to find broad application as and in a biological information measurement device for measuring biological information such as blood glucose levels from blood.

The invention claimed is:

1. A biological information measurement device, comprising:
a main body case having a sensor insertion opening into which a biological information measurement sensor is inserted;
a connector that is provided on an inside of the sensor insertion opening inside the main body case, and is electrically connected to the biological information measurement sensor inserted into the sensor insertion opening;
a measurement component electrically connected to the connector;
a cover that is provided to a surface of the main body case and openably and closeably covers the sensor insertion opening; and
an external temperature measurement component that is provided on the surface of the main body case and is openably and closeably covered by the cover after use, is blocked off from outside air by closure of the cover, and is exposed to the outside air by opening of the cover during measurement with the measurement component, and measures a temperature of air outside the main body case,
wherein the external temperature measurement component is provided on a surface different from a surface of the main body case provided with the sensor insertion opening and is provided between the cover and the sensor insertion opening on the surface of the main body case, and
the cover opens and closes the sensor insertion opening and the external temperature measurement component simultaneously.

2. The biological information measurement device according to claim 1,
wherein the sensor insertion opening and the external temperature measurement component are provided at different locations on the surface of the main body case.

3. The biological information measurement device according to claim 1,
wherein the external temperature measurement component has:
an external temperature measurement opening provided to the surface of the main body case; and
an external temperature measurement sensor provided on an inside of the external temperature measurement opening.

4. The biological information measurement device according to claim 3, wherein the cover shuts the external temperature measurement opening in a state in which the sensor insertion opening has been closed, blocking off the external temperature measurement sensor from the outside air.

5. The biological information measurement device according to claim 1,
wherein a sealing component that covers the sensor insertion opening is formed on a front end side of the cover, and
the cover is linked to the main body case slidably with respect to the surface of the main body case.

6. The biological information measurement device according to claim 1,
wherein the cover is provided rotatably with respect to the main body case, and
the main body case has a stopper that stops the cover in a state of being opposite the external temperature measurement opening at a specific gap.

7. The biological information measurement device according to claim 1, having:
a determination component that determines whether or not the temperature sensed by the external temperature measurement component is changing, prior to measurement with the measurement component; and
a setting component that imposes a measurement-impossible period, in which measurement with the measurement component is impossible, when it has been determined that the sensed temperature is changing.

8. The biological information measurement device according to claim 7,
wherein the determination component has:
a calculator that calculates an amount of temperature change per unit of time from a plurality of sensed temperatures sensed by the external temperature measurement component; and
a comparator that compares the calculated temperature change amount with a reference value for determining whether or not the temperature sensed by the external temperature measurement component is changing, and thereby determines whether or not the sensed temperature is changing.

9. The biological information measurement device according to claim 8,
wherein the setting component enables measurement with the measurement component when it is has been determined by the comparator that the sensed temperature is not changing.

10. The biological information measurement device according to claim 7,
wherein the setting component is connected to a display, and
the setting component causes the display to display a message to an effect that measurement is impossible during the measurement-impossible period.

11. The biological information measurement device according to claim 7,
wherein the determination component sets a temperature range at which the measurement component will perform its measurement, and determines whether or not the temperature sensed by the external temperature measurement component is changing, within this temperature range.

12. A method for controlling a biological information measurement device that comprises:
a main body case having a sensor insertion opening into which a biological information measurement sensor is inserted;
a connector that is provided on an inside of the sensor insertion opening inside the main body case, and is electrically connected to the biological information measurement sensor inserted into the sensor insertion opening;
a measurement component electrically connected to the connector;
a cover that is provided to a surface of the main body case and openably and closeably covers the sensor insertion opening; and
an external temperature measurement component that is provided on the surface of the main body case and is openably and closeably covered by the cover after use, is blocked off from outside air by the closure of the cover, and is exposed to the outside air by the opening of the cover during measurement with the measurement component, and measures temperature of air outside the main body case,
wherein the external temperature measurement component is provided on a surface different from a surface of the main body case provided with the sensor insertion opening and is provided between the cover and the sensor insertion opening on the surface of the main body case, and
the cover opens and closes the sensor insertion opening and the external temperature measurement component simultaneously,
said method comprising:
a determination step of determining whether or not the temperature sensed by the external temperature measurement component is changing, prior to measurement with the measurement component; and
a setting step of imposing a measurement-impossible period in which measurement with the measurement component is impossible, when it has been determined that the sensed temperature is changing.

13. The biological information measurement device according to claim 1,
wherein the cover comprises a first portion covering the external temperature and a second portion covering the sensor insertion opening when the cover closes the sensor insertion opening and the external temperature measurement component, and
the external temperature measurement component are provided between the first portion and the sensor insertion opening.

14. The method for controlling the biological information measurement device according to claim 12,
wherein the cover comprises a first portion covering the external temperature and a second portion covering the sensor insertion opening when the cover closes the sensor insertion opening and the external temperature measurement component, and
the external temperature measurement component are provided between the first portion and the sensor insertion opening.

* * * * *